US010251964B2

(12) United States Patent
Drmanovic (10) Patent No.: US 10,251,964 B2
(45) Date of Patent: Apr. 9, 2019

(54) SELF-DISINFECTING NEEDLELESS DEVICE (71) Applicant: Zoran Drmanovic, Palm City, FL (US)

(72) Inventor: Zoran Drmanovic, Palm City, FL (US)

(73) Assignee: DRMA GROUP INTERNATIONAL LLC, Palm City, FL (US)

( * ) Notice: Subject to any disclaimer, the term of this patent is extended or adjusted under 35 U.S.C. 154(b) by 253 days.

(21) Appl. No.: 15/244,022

(22) Filed: Aug. 23, 2016

(65) Prior Publication Data
US 2018/0055962 A1 Mar. 1, 2018

(51) Int. Cl.
| | |
|---|---|
| *A61L 2/00* | (2006.01) |
| *A61M 1/00* | (2006.01) |
| *A61K 9/02* | (2006.01) |
| *B08B 9/00* | (2006.01) |
| *A61L 2/18* | (2006.01) |
| *A61M 39/16* | (2006.01) |
| *A61L 2/26* | (2006.01) |

(52) U.S. Cl.
CPC .................. *A61L 2/18* (2013.01); *A61L 2/26* (2013.01); *A61M 39/16* (2013.01); *A61M 39/162* (2013.01); *A61L 2202/15* (2013.01); *A61L 2202/24* (2013.01)

(58) Field of Classification Search
CPC ... A61L 2/02; A61L 2/23; A61L 2/186; A61L 2/18; A61B 19/34
USPC ............... 422/28, 292, 300; 134/6, 22.1, 84; 604/905, 288.01, 28
See application file for complete search history.

(56) References Cited

U.S. PATENT DOCUMENTS

| | | | |
|---|---|---|---|
| 2,400,722 A | 5/1946 | Swan | |
| 4,340,052 A | 7/1982 | Dennehey et al. | |
| 4,440,207 A | 4/1984 | Genatempo et al. | |
| 4,919,658 A * | 4/1990 | Badia | A61M 5/162 604/199 |
| 5,053,003 A | 10/1991 | Dadson et al. | |
| 5,242,425 A | 9/1993 | White et al. | |
| 5,295,975 A | 3/1994 | Lockwood, Jr. | |

(Continued)

FOREIGN PATENT DOCUMENTS

| | | |
|---|---|---|
| EP | 0409180 A1 | 1/1991 |
| EP | 0520930 A1 | 12/1992 |

(Continued)

*Primary Examiner* — Monzer R Chorbaji
(74) *Attorney, Agent, or Firm* — Cantor Colburn LLP (57) ABSTRACT

A device for automatically disinfecting a portion of a medical implement. The device includes a reservoir chamber having a top external opening, a medical implement protruded through a bottom part of the reservoir chamber with the portion to be disinfected exposed inside the reservoir chamber and below the top external opening, two disinfecting pads, and a resilient device. Each disinfecting pad is connected to the reservoir chamber through a mounting member, which permits displacement of the disinfecting pads relative to the reservoir chamber in substantially opposite directions thereby creating a gap between each pad and the portion to be disinfected. The resilient device biases the disinfecting pads such that when the disinfecting pads are displaced from a rest position, wherein they are contacting the portion to be disinfected, to an engaged position, the disinfecting pads are urged to return toward the portion to be disinfected to contact and disinfect the portion.

19 Claims, 4 Drawing Sheets

(56) References Cited

U.S. PATENT DOCUMENTS

| | | |
|---|---|---|
| 5,324,264 A | 6/1994 | Whitaker |
| 5,429,612 A | 7/1995 | Berthier |
| 5,681,283 A | 10/1997 | Brownfield |
| 5,792,120 A | 8/1998 | Menyhay |
| 5,885,249 A | 3/1999 | Irisawa |
| 6,045,539 A | 4/2000 | Menyhay |
| 6,171,287 B1 | 1/2001 | Lynn et al. |
| 6,322,540 B1 | 11/2001 | Grabis et al. |
| 6,391,003 B1 | 5/2002 | Lesch, Jr. |
| 6,409,706 B1 | 6/2002 | Loy |
| 6,547,764 B2 | 4/2003 | Larsen et al. |
| 6,582,408 B1 | 6/2003 | Buch-Rasmussen et al. |
| 6,908,460 B2 | 6/2005 | Distefano |
| 7,682,561 B2 * | 3/2010 | Davis ............ A61L 2/18 422/28 |
| 7,815,611 B2 | 10/2010 | Giambattista et al. |
| 7,931,877 B2 | 4/2011 | Steffens et al. |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,298,196 B1 | 10/2012 | Mansour |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,491,546 B2 | 7/2013 | Hoang et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,734,384 B2 | 5/2014 | Boyd et al. |
| 8,740,864 B2 | 6/2014 | Hoang et al. |
| 8,784,388 B2 | 7/2014 | Charles et al. |
| 8,961,475 B2 | 2/2015 | Solomon et al. |
| 8,999,073 B2 * | 4/2015 | Rogers .............. A61B 19/34 134/115 R |
| 9,039,989 B2 | 5/2015 | Liu et al. |
| 9,079,692 B2 | 7/2015 | Solomon et al. |
| 9,114,915 B2 | 8/2015 | Solomon et al. |
| 9,186,707 B2 | 11/2015 | Vaillancourt et al. |
| 9,192,449 B2 | 11/2015 | Kerr et al. |
| 9,259,284 B2 | 2/2016 | Rogers et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 2008/0177250 A1 | 7/2008 | Howlett et al. |
| 2009/0137969 A1 | 5/2009 | Colantonio et al. |
| 2009/0307449 A1 | 12/2009 | Prahlad et al. |
| 2010/0272379 A1 | 10/2010 | Hu et al. |
| 2011/0054440 A1 | 3/2011 | Lewis |
| 2012/0302970 A1 | 11/2012 | Tennican |
| 2013/0171030 A1 | 7/2013 | Ferlic et al. |
| 2015/0360021 A1 | 12/2015 | Limdico et al. |
| 2017/0232121 A1 | 8/2017 | Chiu et al. |
| 2018/0064604 A1 | 3/2018 | Drmanovic |
| 2018/0085568 A1 | 3/2018 | Drmanovic |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

* cited by examiner

SELF-DISINFECTING NEEDLELESS DEVICE

BACKGROUND

The present invention generally relates to a needleless device having self-disinfecting properties, and more specifically, to a self-disinfecting needleless hub or injection port.

Presence of intravenous catheters is the major risk factor for the development of bloodstream infections. These catheters can be either central or peripheral. Needleless hub connectors are ordinarily used as an injection port on the catheters. A typical connector includes a female luer lock, and usually, a syringe with a male luer lock is used to inject fluids or medications.

Needleless hub connector contamination is a major risk factor for bloodstream infection. Scrubbing the female luer lock with alcohol for 10-60 seconds is recommended before each use, but this procedure is often omitted by medical professionals. Studies have shown better results in reducing infection with different types of alcohol impregnated protectors, such as Swab Cap®. However, because the protector constitutes a separate entity, only the most diligent medical professionals would utilize them after every step. In addition, the cap does not assure mandatory compliance. Caps do not always engage the threads on the hub, and the threads can serve as a source of infection, especially, if a dirty or bloody male luer from the syringe is used to engage the hub. Also, because of their small size, the caps are easily contaminated after use if they are placed on a contaminated surface.

Attempts have been made to cover the hub in order to keep it disinfected. However, these efforts either failed to cover the hub completely by shielding only the top membrane, or were too difficult to remove when the port needed to be injected quickly and conveniently.

Thus, there remains a need for a convenient and reliable disinfecting device that would guarantee 100% compliance of medical professionals with antiseptic techniques.

SUMMARY

A device for automatically disinfecting a portion of a medical implement is provided. The device includes a reservoir chamber having a top external opening, a medical implement protruded through a bottom part of the reservoir chamber with the portion to be disinfected exposed inside the reservoir chamber and below the top external opening, two disinfecting pads, and a resilient device. Each disinfecting pad is connected to the reservoir chamber through a mounting member, which permits displacement of the disinfecting pads relative to the reservoir chamber in substantially opposite directions thereby creating a gap between each pad and the portion to be disinfected. The resilient device biases the disinfecting pads such that when the disinfecting pads are displaced from a rest position, wherein they are contacting the portion to be disinfected, to an engaged position, the disinfecting pads are urged to return toward the portion to be disinfected to contact and disinfect the portion.

The reservoir chamber and the medical implement may be permanently affixed to each other so as to form a single entity. In another embodiment, however, the reservoir chamber and the medical implement may not be permanently affixed.

The portion to be disinfected may be a needleless hub or an injection port. The needleless hub may include a female luer fitting and an injection membrane.

Each mounting member may include a sliding panel and a handle attached to the sliding panel. The sliding panels may displace laterally relative to the reservoir chamber in substantially opposite directions.

The resilient device may include a spring or an elastic band connecting each mounting member to an area located on an internal wall of the reservoir chamber.

Each mounting member may further include a supportive panel attached to the sliding panel in a direction substantially perpendicular to the sliding panel. A substantial portion of the supportive panel may be located inside the reservoir chamber without contacting the bottom part of the reservoir chamber.

The spring or the elastic band may connect the supportive panel of each mounting member to an internal wall of the reservoir chamber. The internal wall of the reservoir chamber may fully encircle the portion of the medical implement to be disinfected, and the springs or the elastic bands may be attached to the diametrically opposed areas of the internal wall.

In the rest position, the pads may directly contact each other to completely cover the portion to be disinfected. In the engaged position, the portion to be disinfected may be completely uncovered.

A top portion of each disinfecting pad may be attached to a bottom portion of the corresponding mounting member.

A disinfecting agent may be disposed inside the reservoir chamber. The disinfecting pads may be soaked with the disinfecting agent.

In another embodiment, a device for automatically disinfecting a portion of a medical implement is provided. The device includes a reservoir chamber having a top external opening and a bottom part configured to be engaged with a medical implement having a portion to be disinfected, two disinfecting pads, and a resilient device. Each pad is connected to the reservoir chamber through a mounting member, which permits displacement of the disinfecting pads relative to the reservoir chamber in substantially opposite directions thereby creating a gap between each pad and the portion to be disinfected. The resilient device biases the pads such that when the pads are displaced from a rest position, wherein they are contacting the portion to be disinfected, to an engaged position, the pads are urged to return toward the portion to be disinfected to contact and disinfect the portion.

In yet another embodiment, a method for automatically disinfecting a portion of a medical implement is provided. The method includes providing a device including a reservoir chamber having a top external opening, a medical implement protruded through a bottom part of the reservoir chamber with the portion to be disinfected exposed inside the reservoir chamber and below the top external opening, two disinfecting pads, and a resilient device. Each pad is connected to the reservoir chamber through a mounting member, which permits displacement of the disinfecting pads relative to the reservoir chamber in substantially opposite directions thereby creating a gap between each pad and the portion to be disinfected. The resilient device biases the pads such that when the pads are displaced from a rest position, wherein they are contacting the portion to be disinfected, to an engaged position, the pads are urged to return toward the portion to be disinfected to contact and disinfect the portion. The method further includes displacing the pads from the rest position to the engaged position to expose the disinfected portion of the medical implement through the top external opening of the reservoir chamber; and attaching a source of fluid to the medical implement.

The method may still further include: injecting the fluid into the medical implement, detaching the source of fluid from the medical implement, and displacing the pads from the engaged position to the rest position to bring the pads back in contact with the portion of the medical implement to be disinfected.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within ±30%, 20%, 10%, 5% of the stated value.

In an embodiment, a device for automatically disinfecting a portion of a medical implement is provided. The device includes a reservoir chamber having a top external opening, a medical implement protruded through a bottom part of the reservoir chamber with the portion to be disinfected exposed inside the reservoir chamber and below the top external opening, two disinfecting pads, and a resilient device. Each disinfecting pad is connected to the reservoir chamber through a mounting member, which permits displacement of the disinfecting pads relative to the reservoir chamber in substantially opposite directions thereby creating a gap between each pad and the portion to be disinfected. The resilient device biases the disinfecting pads such that when the disinfecting pads are displaced from a rest position, wherein they are contacting the portion to be disinfected, to an engaged position, the disinfecting pads are urged to return toward the portion to be disinfected to contact and disinfect the portion.

An example of the device for automatically disinfecting a portion of a medical implement according to the above embodiment is shown in FIGS. 1-8. Referring to FIGS. 1-8, a device 100 may include a disinfecting apparatus 101 permanently affixed to a needleless hub 102. The disinfecting apparatus 101 includes three major components: a reservoir chamber 103 and two top covers 104a and 104b. The reservoir chamber 103 may be shaped in such a way that it fully encircles the top portion of the needleless hub connector 102 where female luer threads 105 and an injection membrane 106 are located. Inside the reservoir chamber 103, there are two disinfecting pads 107a and 107b soaked with a disinfecting agent 108. In a rested position shown in FIG. 2, the disinfecting pads 107a and 107b come within close contact with the injection membrane 106 and the threads 105 of the top portion of the hub 102 to disinfect the membrane. One purpose of the top covers 104a and 104b is to serve as a mechanical barrier to prevent a loss of the disinfecting agent 108 by spillage or evaporation. In addition, the lateral movement of the top covers 104a and 104b causes the disinfecting pads 107a and 107b to be displaced so that the top portion of the hub 102 may be exposed and accessed for injection.

A top portion of the disinfecting pads 107a and 107b may be attached to the corresponding top covers 104a and 104b, so that they may move together. A lateral portion of the disinfecting pads 107a and 107b may be attached to the corresponding supportive walls 109a and 109b, which are made of rigid but lightweight material. The supportive walls 109a and 109b may be connected to the disinfecting pads 107a and 107b through extension springs 110a and 110b, and may help the corresponding extension springs 110a and 110b on the same side push flexible disinfecting pads 107a and 107b toward their rested, biased position in close contact with the area of the hub 102 to be disinfected. The light pressure that the top portion of the hub 102 would apply to the disinfecting pads 107a and 107b would cause compression of the pads and release of the disinfecting agent 108 onto the injection membrane 106 and the female luer threads 105. The extension springs 110a and 110b may be attached to one side of the lateral walls 124a and 124b of the reservoir chamber 103 and to the other side of the corresponding supportive walls 109a and 109b. The extension springs 110a and 110b are biased to push the disinfecting pads 107a and 107b toward the top portion of the hub 102 and the female luer threads 105. This movement also pushes the top covers 104a and 104b toward their resting position, thereby closing the apparatus 101 and protecting an injection port of the hub 102. Each of the top covers 104a and 104b may contain side handles 111a and 111b or downward protrusions (not shown) in order to facilitate the lateral displacement (spreading) of the top covers 104a and 104b and the opening of the apparatus 101, wherein the top of the hub 102 may be accessed for injection. A medical provider could hold the body of the hub 102 in one hand and use his or her thumb and forefinger to spread the side handles 111a and 111b apart to expose the top portion of the hub 102 for the injection. The provider may keep the side handles 111a and 111b spread until the injection is complete, and then, let the handles go toward their resting position. The provider may use his or her other hand to hold a syringe and inject medication through the exposed hub 102. After the injection, the provider may release the side handles 111a and 111b so that the top covers 104a and 104b would come together and shield the top portion of the hub 102.

Figure 1:
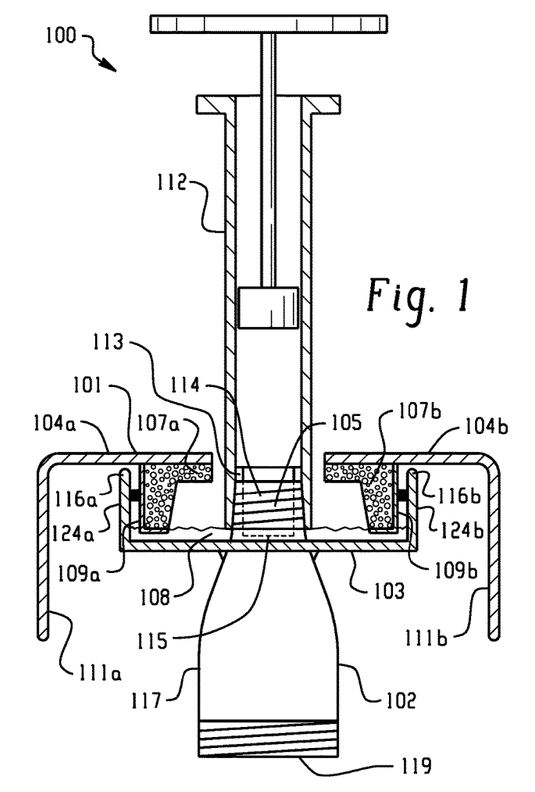
FIG. 1 is a side view of an embodiment of the invention, wherein the top covers are displaced so that a needleless hub with its female luer threads is connected to the male luer threads from the syringe allowing the injection of medication.

FIG. 1 shows a side view of the disinfecting apparatus 101 with the top covers 104a and 104b open and with the top portion of the hub 102 engaged with a syringe 112. The syringe 112 may be any syringe known in the art, and will not be described here. The distal portion 113 of the syringe 112 contains male luer threads 114, while the top portion of the hub 102 contains complementary female luer threads 105. The syringe tip 115 is shown inside the top portion of the hub 102 after pushing the injection membrane 106 of the hub 102 inside. This opens a fluid pathway so that the medication from the syringe 112 may enter the patient's bloodstream via the needleless hub 102. It is important to note that the opening of the top covers 104a and 104b created by spreading of the side handles 111a and 111b provides sufficient room for all common type of devices that may access the hub 102 to fit inside the reservoir chamber 103 and connect with the female luer threads 105 and the injection membrane 106. FIG. 1 also shows the side handles 111a and 111b which may be displaced laterally in substantially opposite directions, usually with a thumb and a forefinger from the same hand or in any other way. This move causes the disinfecting pads 107a and 107b to move laterally in substantially opposite directions away from the top portion of the hub 102. The same move causes the top covers 104a and 104b to move laterally in substantially opposite directions together with the disinfecting pads 107a and 107b because the disinfecting pads 107a and 107b are attached to the corresponding top covers 104a and 104b with their superior surface. Displacement of the top covers 104a and 104b also opens the apparatus 101 for injection access. The extension springs 110a and 110b are both shown in their flexed position in between the lateral walls 124a and 124b of the reservoir chamber 103 and the supportive walls 109a and 109b. The disinfecting pads 107a and 107b are soaked with the disinfecting agent 108, and there is also a small amount of the disinfecting agent present at the bottom of the reservoir chamber 103. It is therefore important that there is a minimal space between superior edges 116a and 116b of the lateral walls 124a and 124b and the top covers 104a and 104b to minimize the loss of the disinfecting agent. At the same time, one should make sure that there is sufficient space to allow smooth sliding of the top covers 104a and 104b laterally. One may find it helpful to place a rubber membrane or a thin sponge near that space to prevent spillage without obstructing lateral displacement of the top covers 104a and 104b.

Figure 2:
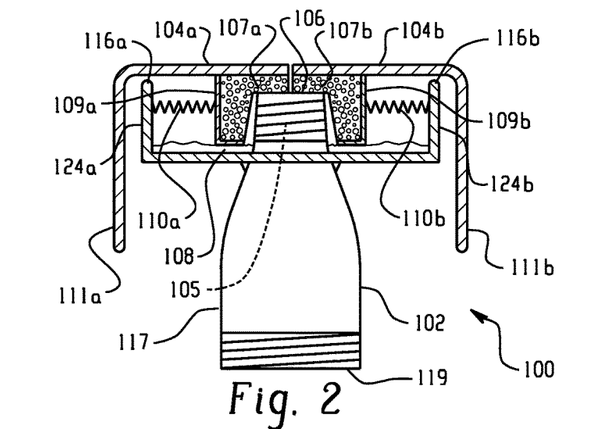
FIG. 2 is a side view of an embodiment of the invention but with top covers and disinfecting pads at a rested position in close contact with the area of the hub to be disinfected.

FIG. 2 shows the disinfecting apparatus 101 in a closed, rested position when it is not in use. After injecting the medication, the medical provider may disconnect the syringe tip 115 and release the side handles 111a and 111b. At that time, the extension springs 110a and 110b would push the corresponding disinfecting pads 107a and 107b and the top covers 104a and 104b toward their rested, biased position at the top of the injection membrane 106 and around the female luer threads 105 thereby disinfecting and preparing them for another use later on. The disinfecting pads 107a and 107b may be made of a non-woven material or a sponge including polyester, silicone, cotton, polyurethane, or any other suitable material. The amount of the material for the disinfecting pads 107a and 107b may vary. The pads may be soaked with any disinfecting agent, which is known to possess antiseptic, antibacterial, and antiviral properties, for example, povidone iodine, alcohol, chlorhexidine, or any combination thereof. It is important that the top covers 104a and 104b match each other very well so that they close tightly and prevent loss of the disinfecting agent either by spillage or evaporation. Thus, a good seal here would also prevent introduction of the infection through the opening. A good seal between the superior edges 116a and 116b of the lateral walls 124a and 124b and the top covers 104a and 104b would be important for the same reason. Since both supportive walls 109a and 109b and the disinfecting pads 107a and 107b are attached to (hanging from) the top covers 104a and 104b, they do not touch the bottom of the reservoir chamber 103. This prevents scratching of the bottom of the reservoir chamber 103, and also permits free movement of the small amount of the disinfecting agent 108 at the bottom of the reservoir chamber 103. In case of an accidental loss of the disinfecting agent 108 by evaporation or spillage, the medical provider can open the disinfecting apparatus 101 and pour a small additional amount of the disinfecting agent 108 into the reservoir chamber 103. The disinfecting pads 107a and 107b are designed to complement each other to completely cover the injection membrane 106, and to completely encircle and come in intimate contact with the top portion of the hub's female luer threads 105. The design of any medical connection hub 102 is well known, and therefore, will not be described in detail here. For the purpose of this disclosure, only parts of the hub 102 related to the present inventive concept will be mentioned. The hub 102 contains a body 117, the top portion with female luer threads 105 disposed around the body 117, and the injection membrane 106 disposed at the top of the body 117. The injection membrane 106 is flexible and may be pushed down by the syringe tip (not shown). A firm rigid rim 118 may be disposed around the injection membrane 106. At the bottom of the hub 102, there may be male luer threads (not shown) designed to connect a distal portion of the hub 119 to any type of intravenous catheter (not shown).

Figure 3:
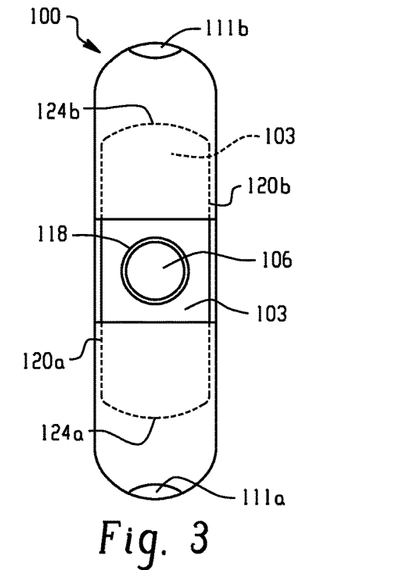
FIG. 3 is a top view of an embodiment of the invention with top covers displaced laterally exposing the hub's access point.

FIG. 3 is a top view of the disinfecting apparatus 101 with the top covers 104a and 104b displaced laterally to expose the top portion of the hub 102 for connection with a syringe 112 and injection of medication. As previously mentioned, in order for the hub 102 to be exposed, the medical provider must laterally displace the side handles 111a and 111b. The figure shows a top view of the hub 102 having the injection membrane 106 in the middle and a top rim 118 disposed around it. Also, around the top portion of the hub 102, the disposed reservoir chamber 103 looks empty because both disinfecting pads 107a and 107b have been displaced laterally together with the top covers 104a and 104b. This allows enough room for the syringe 112 to enter the top part of the reservoir chamber 103 to connect with the top portion of the hub 102. A small amount of the disinfecting agent 108 may be present at the bottom of the reservoir chamber 103. The dotted line defines the part of the reservoir chamber 103 which cannot be seen because it is covered with the top covers 104a and 104b. The reservoir chamber has two lateral walls 124a and 124b situated opposite to each other, and two medial (long) walls 120a and 120b located opposite to each other. In this view, only the top portion of the side handles 111a and 111b is visible laterally on both opposing ends of the disinfecting apparatus 101.

Figure 4:
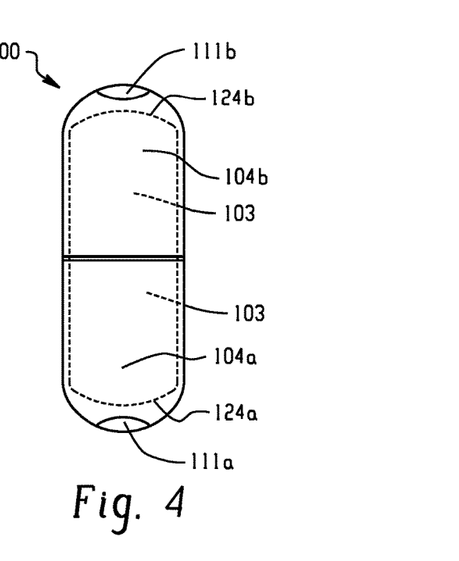
FIG. 4 is a top view of an embodiment of the invention, wherein the top covers are in a resting position with the top portion of the hub completely covered and protected.

FIG. 4 is a top view of the disinfecting apparatus 101 in a rested position with the top covers 104a and 104b closed. This takes place when the medical provider releases the side handles 111a and 111b and the apparatus 101 closes until a subsequent use. The dotted line defines the reservoir chamber 103 which cannot be seen because of the closed top covers 104a and 104b. In this position, the top portion of the hub 102 is well protected and is completely covered with the disinfecting pads 107a and 107b (not seen in this view). The top covers are slightly longer laterally compared to the reservoir chamber 103 to accommodate for the diameter of the side handles 111a and 111b.

Figures 5, 7:
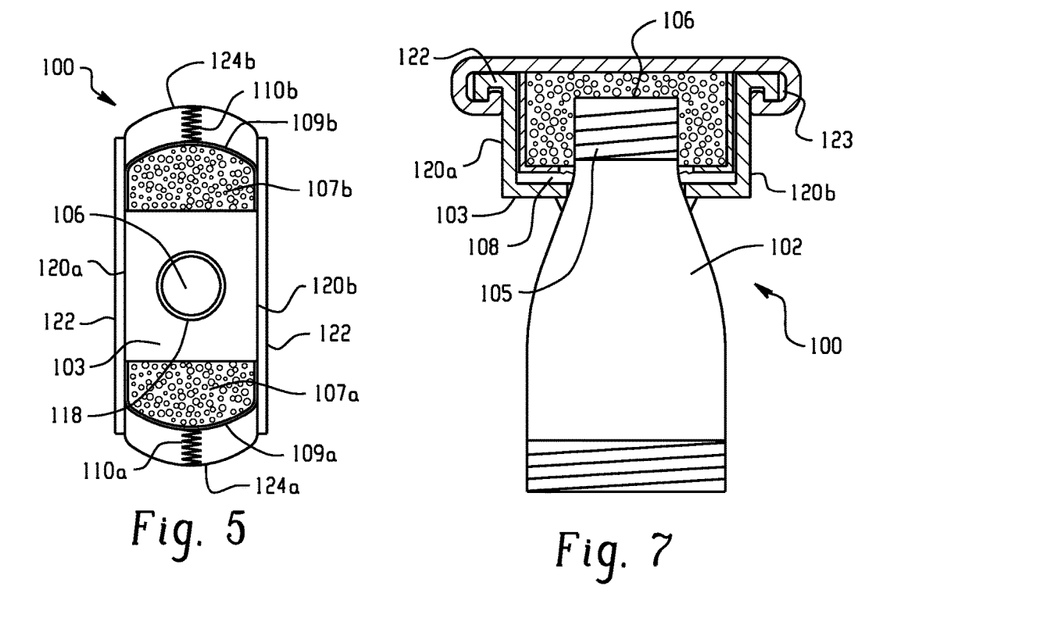
FIG. 5 is a top view of an embodiment of the invention shown without the top covers but with the disinfecting pads displaced so that the hub's access point is exposed.
FIG. 7 is a cross-sectional view of an embodiment of the invention showing the top of the hub covered with the disinfecting pad and a ridge on both sides of the reservoir chamber which keeps the top covers and the reservoir chamber together.

FIG. 5 is the top view of the disinfecting apparatus 101, which is shown without the top covers 104a and 104b. The figure shows what the reservoir chamber 103 looks like from the top when the disinfecting pads 107a and 107b are displaced in substantially opposite directions, and when the top portion of the hub 102 is exposed for the injection. The extension springs 110a and 110b are shown to be in a flexed mode and are attached to the corresponding lateral walls 124a and 124b of the reservoir chamber 103 and medially to the corresponding supportive walls 109a and 109b. The medial walls 120a and 120b of the reservoir chamber 103 have a ridge 122 disposed at the top of the walls, which is used to connect to the top covers 104a and 104b. In this view, the injection membrane 106 and the rim 118 around it are exposed. There is sufficient room around the top portion of the hub 102 in the reservoir chamber 103 to accommodate a syringe 112 for injection of a medication.

Figure 6:
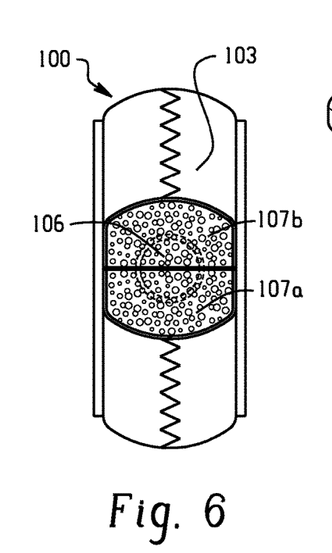
FIG. 6 is a top view of an embodiment of the invention shown without the top covers but with the disinfecting pads completely covering the hub's access point and the side threads.

Similarly to the view in FIG. 5, FIG. 6 shows the disinfecting apparatus 101 without the top covers 104a and 104b but with the disinfecting pads 107a and 107b in a rested, biased position completely covering the injection membrane 106 (shown with the dotted lines). The disinfecting pads 107a and 107b are in intimate contact with the female luer threads 105 (not seen in this view) to disinfect them because the pads are soaked in the disinfecting agent, while a small amount of the agent 108 (not seen in this view) also covers the floor of the reservoir chamber 103. The movement (for example, shaking) of the apparatus may cause the extra amount of the disinfecting agent to spread all over the reservoir chamber 103 and re-soak the disinfecting pads 107a and 107b.

FIG. 7 is a cross-sectional view of the device which shows the top portion of the hub 102 with the female luer threads 105. The disinfecting pads 107a and 107b completely cover the injection membrane 106 and are contacting the female luer threads 105. The medial walls 120a and 120b are shown with the ridge 122 disposed at the top of them. The top covers 104a and 104b are also shown with their sides bent to create a canal 123 which accepts the complementary ridge 122. The canal 123 and the ridge 122 serve to keep the top covers 104a and 104b attached to the reservoir chamber 103, and also allow a lateral displacement of the top covers 104a and 104b with the sliding move. The canal 123 and the ridge 122 also define the extreme points of the lateral displacement. Some lubricant may be used inside the canal 123 to allow smoother sliding, and in some variations small wheels (not shown) might be placed there for smooth displacement.

Figure 8:
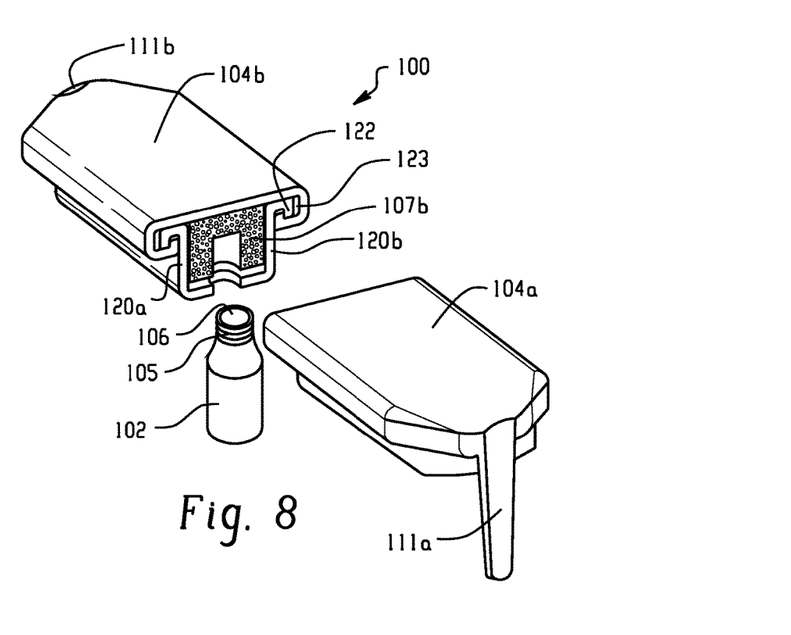
FIG. 8 is also a cross-sectional view of an embodiment of the invention with the top portion of the hub separated from the invention which is also shown cut in two equal parts.

FIG. 8 is cross-sectional tri-dimensional view of the device 100 according to an embodiment. It shows how the apparatus would look when cut in half with the hub 102 disposed in between. This view best shows the shape of the disinfecting pad 107a, which allows it not only to encircle the female luer threads 105, but also to completely cover the injection membrane 106 where injection actually occurs. While some prior art devices only disinfect the injection membrane, the disinfecting apparatus 101, according to the embodiment, also keeps the female luer threads 105 completely covered with the disinfecting pads 107a and 107b. This arrangement ensures better disinfection results as the male luer threads 114 on a syringe (not shown in this view) are often contaminated with bacteria or blood. After connection of the male luer from the syringe with the female luer threads 105 from the hub 102, the blood or bacteria may stay on the female luer threads 105, and from there, spread the contamination to the injection membrane 106. The present device completely prevents this process. FIG. 8 also allows one to see how the canal 123, which is formed from the top covers 104a and 104b on the medial sides, complements the ridge 122 formed by the reservoir chamber's medial walls 120a or 120b, thus allowing a lateral displacement of the top covers 104a and 104b together with the disinfecting pads 107a or 107b. This view also shows the right side handle 111a whose shape and size would allow for an easy lateral displacement and may include some ridges on its surface for easy gripping. Also the distance between the body of the hub 102 and the side handle 111a should be sufficient to allow the thumb and the forefinger of the medical provider to fit in, so that these two fingers could be used to spread (laterally displace the side handles 111a and 111b together with the top covers 104a and 104b and the disinfecting pads 107a or 107b).

In another embodiment, a device for automatically disinfecting a portion of a medical implement is provided. The device includes a reservoir chamber having a top external opening and a bottom part configured to be engaged with a medical implement having a portion to be disinfected, two disinfecting pads, and a resilient device. Each pad is connected to the reservoir chamber through a mounting member, which permits displacement of the disinfecting pads relative to the reservoir chamber in substantially opposite directions thereby creating a gap between each pad and the portion to be disinfected. The resilient device biases the pads such that when the pads are displaced from a rest position, wherein they are contacting the portion to be disinfected, to an engaged position, the pads are urged to return toward the portion to be disinfected to contact and disinfect the portion.

Figure 9:
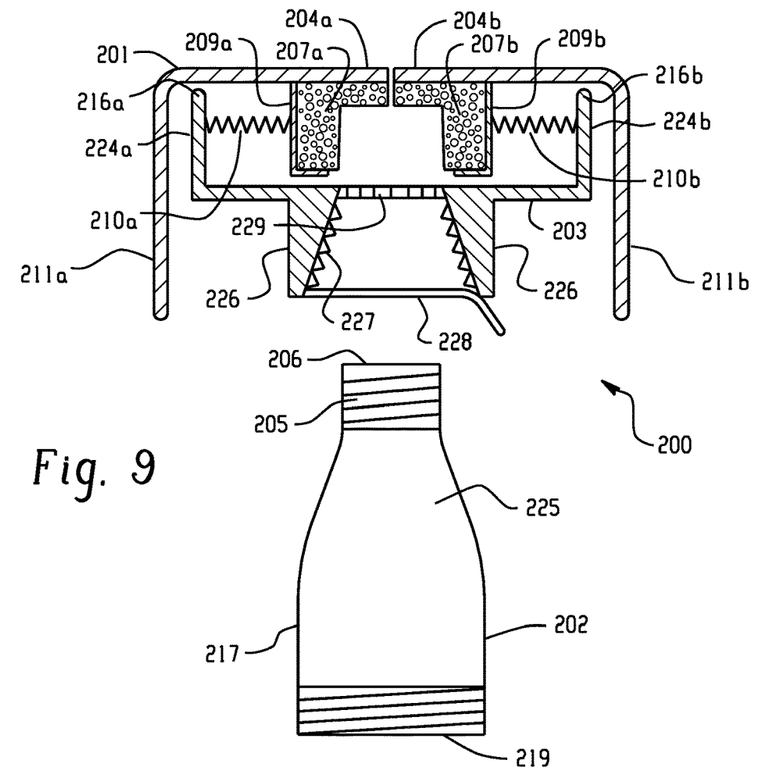
FIG. 9 shows a side view of another embodiment of the invention in a rested position before being attached to a needleless hub.

FIG. 9 shows the cross-sectional view of this embodiment of the self-disinfecting needleless device 200, wherein the disinfecting apparatus 201 is not permanently attached to the hub 202 during the manufacturing process. This embodiment allows the disinfecting apparatus 201 to be added to any connection hub on any intravenous line. An advantage of this embodiment is that the medical provider may choose to attach the disinfecting apparatus to a particular hub, which he or she frequently uses. The view shows the same parts already described in previous figures like top covers 204a and 204b, disinfecting pads covers 207a and 207b, a reservoir chamber 203, supportive walls 209a and 209b, extension springs 210a and 210b, side handles 211a and 211b, and lateral walls 224a and 224b. The view also shows separately one of common connection hubs 202 with the parts such as an injection membrane 206 disposed at the top of the hub 202, female luer threads 205, a neck of the hub 225, a body of the hub 217 and male luer threads 219 located at the bottom of the hub. New elements of the disinfecting apparatus 201 allow it to be attached to the hub 202. These new elements include a funnel 226, which has a shape of an upper part of the most common connection hubs. The funnel 226 may be made from the same rigid but lightweight material as the reservoir chamber 203, but may also allow for small variations in common hub sizes. The funnel 226 may also be of a different length as long as it assures good connection. Some hubs have a small vent (hole) located on their body, and the funnel 226 is not designed to cover the vent. An inner surface of the funnel 226 is covered with an adhesive material 227, which allows for a good connection between the apparatus 201 and the hub 202. At the bottom of the funnel 226 is a removable (peelable) foil 228, which keeps the inner portion of the funnel 226 clean, prevents drying of the adhesive material 227, and represents a fluid barrier. The foil 228 may also provide a visible indication that the seal is broken. A medical professional would peel the foil 228 just before connecting the apparatus with the hub 202. A central portion of the reservoir chamber floor lacks ridged lightweight material, but instead, may be covered with a funnel membrane 229 made of a rubber or some other flexible material. This membrane is designed to prevent the disinfecting agent from entering the funnel 226 at a resting position before the apparatus 201 is connected to the hub 202. The funnel membrane 229 is also designed to allow the top portion of the hub 202 to penetrate the membrane during the connection process, and to create a good seal around the top portion of the hub 202 to prevent a leak of the disinfecting agent into the funnel 226 after the connection to the hub 202. It is recommended to have the apparatus upside down during the connection with the hub 202 to minimize chances of leakage of the disinfecting agent 208 around the top portion of the hub during the connection process before the funnel membrane 229 creates a good seal around it.

Figure 10:
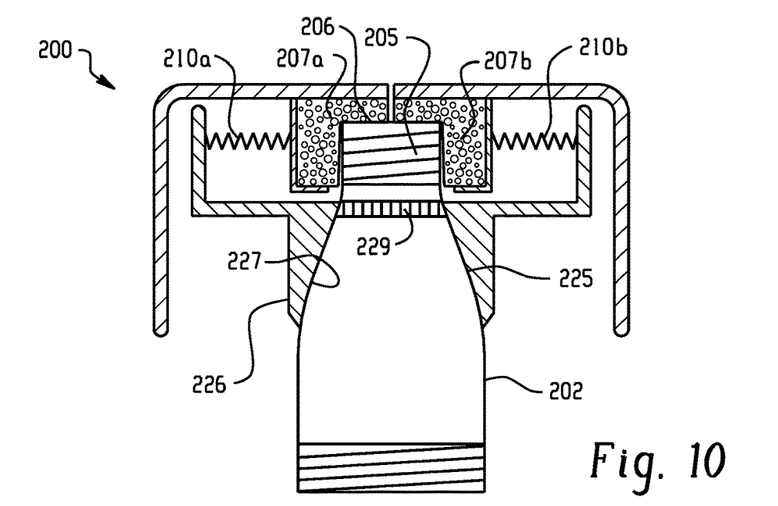
FIG. 10 is also a side view of another embodiment of invention after connecting to the needleless hub.

FIG. 10 shows the disinfecting apparatus after the connection to the hub 202. It is important that the hub 202 is pushed inside enough so that the injection membrane 206 and the female luer threads 205 of the hub come into contact with the disinfecting pads 207a and 207b. The figure also shows the funnel membrane 229 creating a good seal around the top portion of the hub 202, thus preventing leakage of the disinfecting agent 208 into the funnel 226. The adhesive material 227 creates a tight bond with the neck of the hub 225, thus keeping the apparatus and the hub together. It also contributes to the prevention of leakage of the disinfecting agent in case the funnel membrane 229 fails to create a perfect seal. Once the disinfecting apparatus 201 and the hub 202 are well connected, the apparatus would function similarly to what has been previously described.

Figure 11:
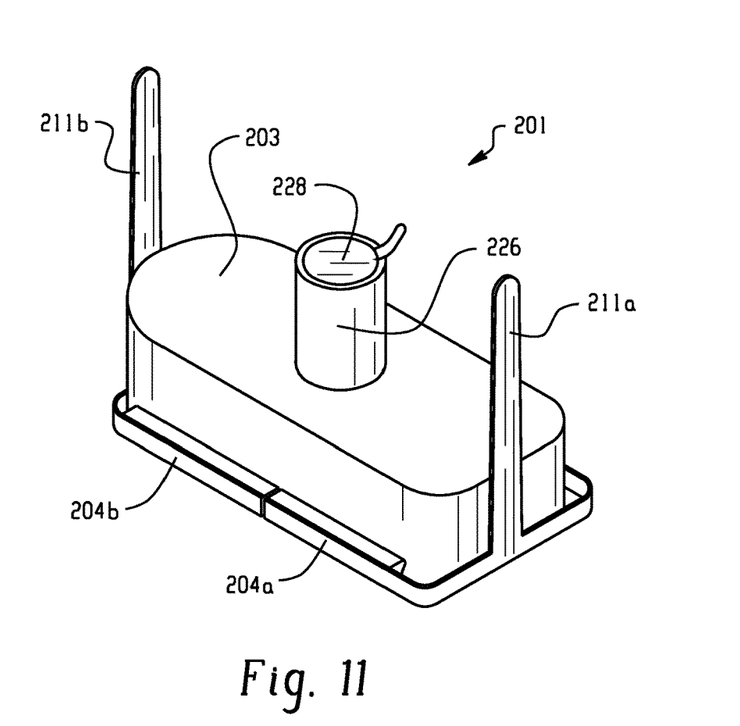
FIG. 11 is a bottom view of another embodiment of the invention before being connected to a needleless hub.

FIG. 11 shows the bottom view of the embodiment of the disinfecting apparatus 201, wherein the funnel 226 and the peelable foil 228 are intact before connecting to the hub 202 (not shown). This is the position in which the apparatus is ready to accept the hub 202 in order to prevent leakage of the disinfecting agent 208 (not shown) during connection process as previously described.

Figure 12:
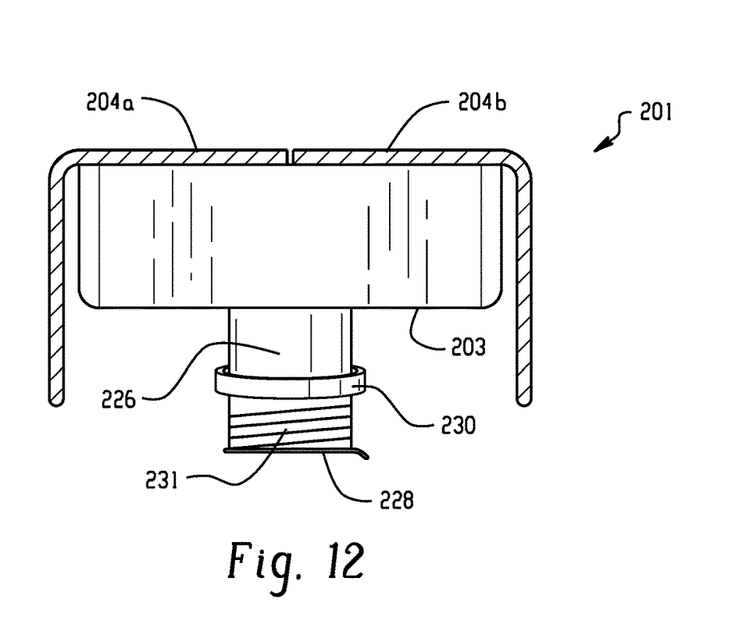
FIG. 12 is a side view of another embodiment of invention with a safety ring disposed around the funnel.

FIG. 12 shows another variation of this embodiment. To ensure a perfect connection between the apparatus 201 and the neck of the hub 202, the funnel 226 not only contains adhesive material 227 (not shown) over its inner surface, but also has a safety ring 230 and threads 231 disposed on it. After attaching the apparatus 201 with the hub 202, a medical provider would connect threads inside the safety ring 230 with the complementary threads 231 on the funnel 226 and tighten them until a perfect connection is achieved. One would also find the safety ring 230 to be helpful as there are different producers of the connection hubs with small difference in the diameter. Everything inside the apparatus 201 would be substantially the same as described in the embodiments above.

In yet another embodiment, a method for automatically disinfecting a portion of a medical implement is provided.

The method includes providing a device including a reservoir chamber having a top external opening, a medical implement protruded through a bottom part of the reservoir chamber with the portion to be disinfected exposed inside the reservoir chamber and below the top external opening, two disinfecting pads, and a resilient device. Each pad is connected to the reservoir chamber through a mounting member, which permits displacement of the disinfecting pads relative to the reservoir chamber in substantially opposite directions thereby creating a gap between each pad and the portion to be disinfected. The resilient device biases the pads such that when the pads are displaced from a rest position, wherein they are contacting the portion to be disinfected, to an engaged position, the pads are urged to return toward the portion to be disinfected to contact and disinfect the portion. The method further includes displacing the pads from the rest position to the engaged position to expose the disinfected portion of the medical implement through the top external opening of the reservoir chamber; and attaching a source of fluid to the medical implement.

The method may still further include: injecting the fluid into the medical implement, detaching the source of fluid from the medical implement, and displacing the pads from the engaged position to the rest position to bring the pads back in contact with the portion of the medical implement to be disinfected.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A device for automatically disinfecting a portion of a medical implement, comprising:
    a reservoir chamber comprising a top external opening;
    a medical implement protruded through a bottom part of the reservoir chamber with the portion to be disinfected exposed inside the reservoir chamber and below the top external opening, wherein the portion to be disinfected comprises an injection membrane and female luer threads;
    two disinfecting pads, each disinfecting pad is in a direct and prolonged contact with the injection membrane and the female luer threads, and each disinfecting pad connected to the reservoir chamber through a mounting member, wherein the mounting members permit displacement of the disinfecting pads relative to the reservoir chamber in substantially opposite directions thereby creating a gap between each pad and the portion to be disinfected; and
    a resilient device biasing the disinfecting pads such that when the disinfecting pads are displaced from a rest position, wherein they are contacting the injection membrane and the female luer threads of the portion to be disinfected, to an engaged position, the disinfecting pads are urged to return toward the portion to be disinfected to contact and disinfect the injection membrane and the female luer threads of the portion.

2. The device according to claim 1, wherein the reservoir chamber and the medical implement are permanently affixed to each other so as to form a single entity.

3. The device according to claim 1, wherein the reservoir chamber and the medical implement are not permanently affixed.

4. The device according to claim 1, wherein the portion to be disinfected is a needleless hub or an injection port.

5. The device according to claim 1, wherein each mounting member comprises a sliding panel and a handle attached to the sliding panel.

6. The device according to claim 5, wherein the sliding panels displace laterally relative to the reservoir chamber in substantially opposite directions.

7. The device according to claim 5, wherein each mounting member further comprises a supportive panel attached to the sliding panel in a direction substantially perpendicular to the sliding panel, wherein a substantial portion of the supportive panel is located inside the reservoir chamber without contacting the bottom part of the reservoir chamber.

8. The device according to claim 7, wherein the spring or the elastic band connects the supportive panel of each mounting member to an internal wall of the reservoir chamber.

9. The device according to claim 8, wherein the internal wall of the reservoir chamber fully encircles the portion of the medical implement to be disinfected, and wherein the springs or the elastic bands are attached to the diametrically opposed areas of the internal wall.

10. The device according to claim 1, wherein the resilient device comprises a spring or an elastic band connecting each mounting member to an area located on an internal wall of the reservoir chamber.

11. The device according to claim 1, wherein in the rest position, the pads directly contact each other to completely cover the portion to be disinfected.

12. The device according to claim 1, wherein in the engaged position, the portion to be disinfected is completely uncovered.

13. The device according to claim 1, wherein a top portion of each disinfecting pad is attached to a bottom portion of the corresponding mounting member.

14. The device according to claim 1, wherein a disinfecting agent is disposed inside the reservoir chamber.

15. The device according to claim 14, wherein the disinfecting pads are soaked with the disinfecting agent.

16. A device for automatically disinfecting a portion of a medical implement, comprising:
    a reservoir chamber comprising a top external opening and a bottom part configured to be engaged with a medical implement comprising a portion to be disinfected, wherein the portion to be disinfected comprises an injection membrane and female luer threads;
    two disinfecting pads, each pad connected to the reservoir chamber through a mounting member, wherein the mounting members permit displacement of the disinfecting pads relative to the reservoir chamber in substantially opposite directions thereby creating a gap between each pad and the portion to be disinfected; and
    a resilient device biasing the pads such that when the pads are displaced from a rest position, wherein they are contacting the injection membrane and the female luer threads of the portion to be disinfected, to an engaged position, the pads are urged to return toward the portion to be disinfected to contact and disinfect the injection membrane and the female luer threads of the portion.

17. A method for automatically disinfecting a portion of a medical implement, comprising:
    providing a device comprising:
        a reservoir chamber comprising a top external opening;
        a medical implement protruded through a bottom part of the reservoir chamber with the portion to be disinfected exposed inside the reservoir chamber and below the top external opening, wherein the portion to be disinfected comprises an injection membrane and female luer threads;

two disinfecting pads, each disinfecting pad is in a direct and prolonged contact with the injection membrane and the female luer threads, and each pad connected to the reservoir chamber through a mounting member, wherein the mounting members permit displacement of the disinfecting pads relative to the reservoir chamber in substantially opposite directions thereby creating a gap between each pad and the portion to be disinfected; and a resilient device biasing the pads such that when the pads are displaced from a rest position, wherein they are contacting the injection membrane and the female luer threads of the portion to be disinfected, to an engaged position, the pads are urged to return toward the portion to be disinfected to contact and disinfect the injection membrane and the female luer threads of the portion, displacing the pads from the rest position to the engaged position to expose the disinfected portion of the medical implement through the top external opening of the reservoir chamber; and attaching a source of fluid to the medical implement.

18. The method according to claim 17, further comprising:

injecting the fluid into the medical implement.

19. The method according to claim 18, further comprising:

detaching the source of fluid from the medical implement; and displacing the pads from the engaged position to the rest position to bring the pads back in contact with the injection membrane and the female luer threads of the portion of the medical implement to be disinfected.

* * * * *